United States Patent
Biffi et al.

(10) Patent No.: US 9,668,818 B2
(45) Date of Patent: Jun. 6, 2017

(54) METHOD AND SYSTEM TO SELECT AN INSTRUMENT FOR LEAD STABILIZATION

(71) Applicant: Medtronic, Inc., Minneapolis, MN (US)

(72) Inventors: Mauro Biffi, Bologna (IT); Eric A. Schilling, Ham Lake, MN (US); Manfred Justen, Lino Lakes, MN (US)

(73) Assignee: Medtronic, Inc., Minneapolis, MN (US)

( * ) Notice: Subject to any disclaimer, the term of this patent is extended or adjusted under 35 U.S.C. 154(b) by 33 days.

(21) Appl. No.: 14/515,083

(22) Filed: Oct. 15, 2014

(65) Prior Publication Data

US 2016/0106512 A1  Apr. 21, 2016

(51) Int. Cl.
| | |
|---|---|
| G06K 9/00 | (2006.01) |
| A61B 19/00 | (2006.01) |
| A61N 1/00 | (2006.01) |
| A61B 34/10 | (2016.01) |
| G06F 19/00 | (2011.01) |
| A61N 1/05 | (2006.01) |

(52) U.S. Cl.
CPC .............. *A61B 19/50* (2013.01); *A61B 34/10* (2016.02); *A61N 1/00* (2013.01); *A61B 2019/505* (2013.01); *A61B 2019/508* (2013.01); *A61B 2576/02* (2013.01); *A61N 1/057* (2013.01); *G06F 19/30* (2013.01); *G06F 19/3437* (2013.01)

(58) Field of Classification Search
None
See application file for complete search history.

(56) References Cited

U.S. PATENT DOCUMENTS

| | | |
|---|---|---|
| 623,518 A | 4/1899 | Crook |
| 6,006,122 A | 12/1999 | Smits |
| 6,285,903 B1 | 9/2001 | Rosenthal et al. |
| 6,623,518 B2 | 9/2003 | Thompson et al. |
| 6,842,644 B2 | 1/2005 | Anderson et al. |
| 6,980,675 B2 | 12/2005 | Evron et al. |
| 7,218,968 B2 | 5/2007 | Condie et al. |
| 7,308,299 B2 | 12/2007 | Burrell et al. |
| 7,321,677 B2 | 1/2008 | Evron et al. |
| 7,327,872 B2 | 2/2008 | Vaillant et al. |
| 7,499,743 B2 | 3/2009 | Vass et al. |
| 7,587,074 B2 | 9/2009 | Zarkh et al. |
| 7,689,014 B2 | 3/2010 | Abovitz et al. |
| 7,697,972 B2 | 4/2010 | Verard et al. |
| 7,742,629 B2 | 6/2010 | Zarkh et al. |
| 7,778,685 B2 | 8/2010 | Evron et al. |
| 7,778,686 B2 * | 8/2010 | Vass ................... A61B 5/0456 600/424 |
| 7,813,785 B2 | 10/2010 | Okerlund et al. |
| 7,991,453 B2 | 8/2011 | Florent et al. |
| 7,996,063 B2 | 8/2011 | Vass et al. |

(Continued)

OTHER PUBLICATIONS

"Attain Left-Heart Leads," LV Leads for CRT Implantation with Biventricular Devices—Medtronic Brochure. (2013). 12 sheets.

(Continued)

*Primary Examiner* — Tahmina Ansari

(57) ABSTRACT

Disclosed is a system to assist in selecting and/or suggesting an instrument for a procedure. The suggestion may be based upon or include analysis of image data of a subject. The instrument may be suggested for placement inside a tubular structure.

22 Claims, 2 Drawing Sheets

(56) References Cited

U.S. PATENT DOCUMENTS

| | | |
|---|---|---|
| 8,025,622 B2 | 9/2011 | Rold et al. |
| 8,052,711 B2 | 11/2011 | Hanse et al. |
| 8,073,213 B2 | 12/2011 | Vaillant et al. |
| 8,298,147 B2 | 10/2012 | Huennekens et al. |
| 8,355,784 B2 | 1/2013 | Rochat et al. |
| 8,401,616 B2 | 3/2013 | Verard et al. |
| 8,483,829 B2 | 7/2013 | Rochat et al. |
| 8,515,527 B2 | 8/2013 | Vaillant et al. |
| 8,731,642 B2 | 5/2014 | Zarkh et al. |
| 2002/0077583 A1* | 6/2002 | Clemens ............ A61M 25/0026 604/19 |
| 2005/0008210 A1 | 1/2005 | Evron et al. |
| 2006/0020314 A1* | 1/2006 | Bodner ............... A61N 1/05 607/116 |
| 2006/0074285 A1 | 4/2006 | Zarkh et al. |
| 2008/0172119 A1* | 7/2008 | Yamasaki ............. A61B 5/06 623/1.11 |
| 2010/0298695 A1 | 11/2010 | Wenger |
| 2011/0054581 A1 | 3/2011 | Desai et al. |
| 2011/0112398 A1 | 5/2011 | Zarkh et al. |
| 2011/0144734 A1 | 6/2011 | Westlund et al. |
| 2011/0208030 A1 | 8/2011 | Stevenson et al. |
| 2011/0213260 A1 | 9/2011 | Keel et al. |
| 2012/0232478 A1 | 9/2012 | Haslinger |
| 2012/0253340 A1 | 10/2012 | Stevenson et al. |
| 2013/0064343 A1 | 3/2013 | Verstraelen et al. |
| 2013/0116739 A1 | 5/2013 | Brada et al. |
| 2014/0330347 A1 | 11/2014 | Simms, Jr. |
| 2014/0371833 A1 | 12/2014 | Ghosh et al. |
| 2015/0104085 A1* | 4/2015 | Schilling ............... A61B 6/463 382/128 |
| 2015/0206302 A1 | 7/2015 | Chen |

OTHER PUBLICATIONS

"Attain® Family Left-Heart Leads and Delivery Systems," Medtronic Brochure. (2004). 6 sheets.

Attain Stability™ Model 20066. Medtronic Brochure. (2013). 4 sheets.

Biffi, Mauro et al. "Left Ventricular Lead Stabilization to Retain Cardiac Resynchronization Therapy at Long Ter: When is it Advisable." Europace Advance Acess (Sep. 26, 2013). (8 pages).

CardioGuide™ Implant System. Medtronic Brochure. (2013). 2 sheets.

U.S. Appl. No. 14/262,027, filed Apr. 25, 2014, Lahm.

Yu et al. "Cardiac Resynchronization Therapy", Wiley-Blackwell; 2 edition (May 12, 2008), pp. 205-207.

U.S. Appl. No. 14/254,288, filed Apr. 16, 2014, Schilling.

U.S. Appl. No. 14/515,083, filed Oct. 15, 2015, Biffi.

* cited by examiner

METHOD AND SYSTEM TO SELECT AN INSTRUMENT FOR LEAD STABILIZATION

FIELD

The subject disclosure is related to a system and method for performing a procedure on a subject, particularly to assisting in selecting an instrument for use.

BACKGROUND

This section provides background information related to the present disclosure which is not necessarily prior art.

A procedure can be performed on a subject according to various methods and using selected systems. For example, an instrument can be positioned within a selected portion of a subject. An instrument can include a catheter, a lead, an implantable medical device, or other selected portions. Generally, selecting the instrument to be positioned within a subject, however, is based upon only a single surgeon's or a limited number of surgeons' analysis.

SUMMARY

This section provides a general summary of the disclosure, and is not a comprehensive disclosure of its full scope or all of its features.

A system can assist in selecting and/or suggesting a selected instrument for a procedure, such as one based upon analysis of data from a subject. A subject, human or non-human, can include a system that has a plurality of structures that may be receive an instrument. For example, a maintenance device may be positioned within a tubing of a heat exchanger. Additionally, an instrument can be positioned within the vasculature of a subject, such as a human subject. The instrument can include a lead that is connected to an implantable medical device for various purposes, such as a cardiac resynchronization device, stimulation device, and the like.

Generally, positioning an instrument within a subject can be based upon analysis of image data of a subject. The image data can be used to generate a model, such as a three-dimensional model or a two-dimensional model. The model can be used to identify various structures and/or analyze structures within the subject, such as by size and geometry. The structures can be used to assist in determining an appropriate instrument and/or placement of the instrument within the subject. Thus, a system can be used for assisting in efficiently selecting an instrument for positioning within a subject.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
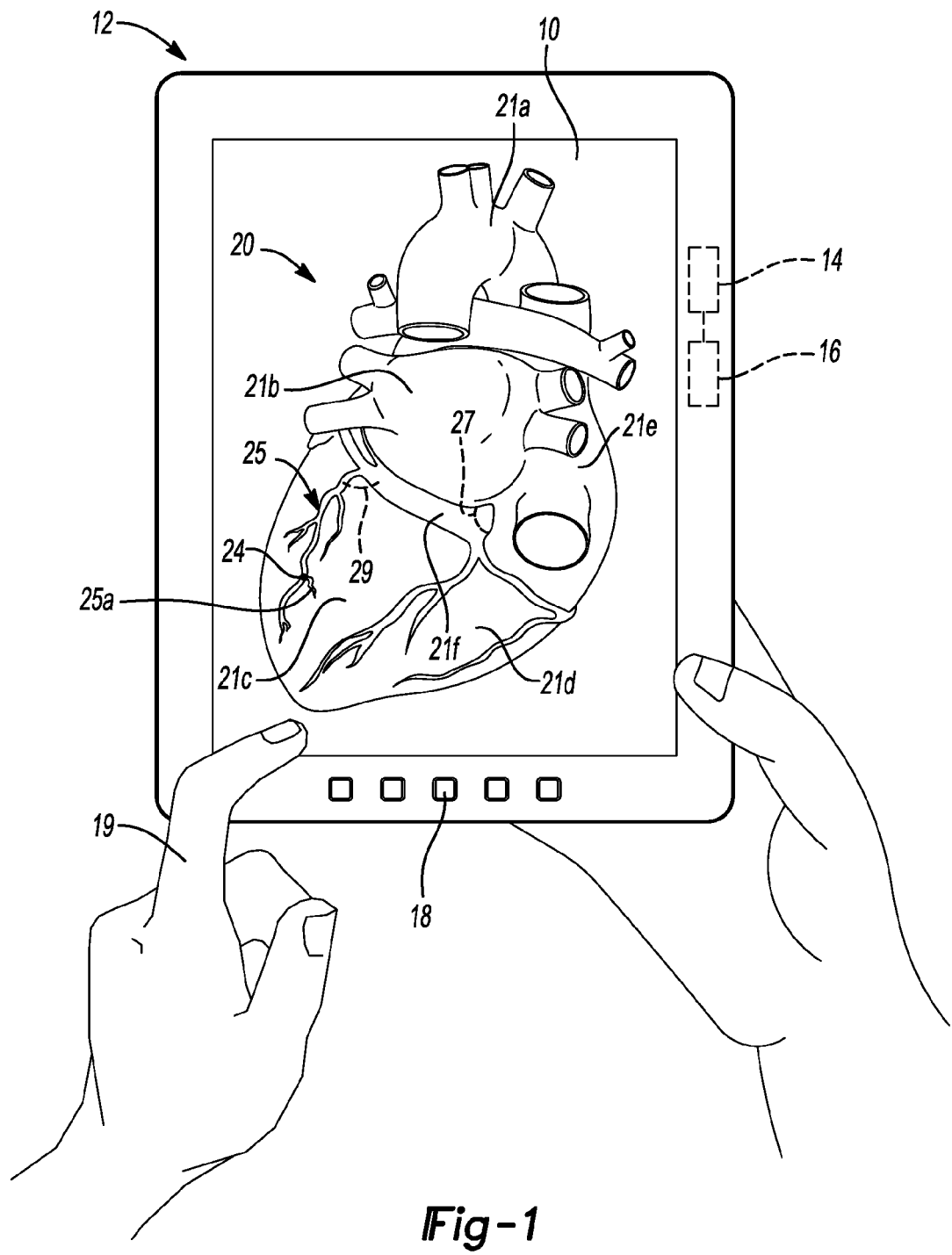
FIG. 1 is a schematic view of an system including a processor.

Example embodiments will now be described more fully with reference to the accompanying drawings.

A user, such as a surgeon or engineer can attempt to select an instrument to be positioned within a tubular structure. For example, a plumber can select an instrument to be positioned within a plumbing line or HVAC system to analyze and/or repair the system. Accordingly, a user may evaluate the geometry of the tubular system, interconnections of tubes in the system, and other information to assist in selecting an appropriate instrument. In various embodiments, a surgeon may use a system to evaluate image data of a subject to assist in determining an appropriate instrument to be positioned within a patient. For example, a model can be created or generated based upon image data of the subject to determine or assist in selecting a lead to be positioned within the subject. For example, a lead for cardiac resynchronization therapy (CRT) can be positioned within a selected portion of a vasculature to assist in resynchronization of a heart muscle. The resynchronization can be based upon or input from an implantable medical device (IMD) and the lead may be selectively positioned, held, and/or fixed at a selected location within the patient.

According to various embodiments, determining an appropriate lead to be positioned within a subject can be based upon various parameters. Further, a subject may include or possess a vasculature that is accessible or appropriate for only a limited number of all possible leads. For example, a passive lead that can be positioned within a subject with minimal trauma to a subject and fixation or holding the lead may be substantially only with "wedging" the lead into the vasculature. In a passive fixation lead, a lead may substantially engage only an interior wall of a vasculature.

An active fixation lead, however, may be selected to assist in maintaining a location of a lead within a subject, this selection may be based upon various parameters. For example, a selected subject may include an anatomy that may be prone to minimizing stabilization of a passive lead based upon various parameters. For example, an active fixation or stabilization system may be selected based upon various geometrical specifics of a subject, such as referenced and discussed in Biffi et al., "Left ventricular lead stabilization to retain cardiac resynchronization therapy at long term: when is it advisable?", European Society of Cardiology, Europace 2014 April; 16 (4):533-40. doi: 10.1093/europace/eut300. Epub 2013 Sep. 26 PMID:24072448 [PubMed—in process]

The following disclosure relates generally to the positioning of a lead within a subject. For example, a lead can be positioned within a subject for a cardiac resynchronization therapy (CRT). It is understood, however, as noted above, that other appropriate instruments can be positioned within various non-anatomical locations for achieving a selected result. For example, an instrument can be positioned within a tubing structure to assist in analyzing an integrity of a tubular structure, repairing a structure, and other appropriate procedures. Accordingly, although the following disclosure relates generally to positioning a lead within a subject, it is understood that a system and method, including those disclosed herein, are not limited to positioning a lead within a subject.

A subject, such as a human subject, however, may include a heart with a selected vasculature. The vasculature of a heart and near a heart may include various vasculature elements that are positioned around and relative to a heart. For example, a coronary sinus (CS) can extend around a portion of an anatomy of the heart and provide blood flow relative to various portions of the heart, including collecting blood from the heart muscle. A coronary sinus can be accessed through a coronary sinus ostium (CSos) within the heart to allow for positioning of a lead relative to a coronary sinus adjacent to a heart.

Coronary veins in a human anatomy can be classified according to various types, including those disclosed in Biffi et al. According to Biffi et al., a type-A vein includes a vein that has an origin between the CSos in a subject and a proximal third of a CS' upward course to a lateral or posterior-lateral pacing site. A type-B vein is a vein that includes a flat take-off from a CS at an angle of greater than 80°. Finally, a type-C vein is any other type of vein that is a vein with a take-off of less than or equal to 80° or a gooseneck take-off from the CS.

Analysis of a subject, such as for determining the type of vein, can be made with a model of the subject based on an image of an anatomy of a subject, as discussed further herein. Images can include image data from a magnetic resonance image (MRI), computed tomography (CT) image data, venogram image data, or other appropriate image data. According to various embodiments, the venogram can be used to acquire image data of a subject. In a venogram, a contrast agent can be passed through a vasculature structure and the anatomy can be imaged with an x-ray imaging system. Various systems can be used to generate and/or analyze the venographic data including the CardioGuide™ Implant System sold by Medtronic, Inc. In various embodiments, the CardioGuide™ Implant System can be used to analyze and/or generate image data of a subject such as venogram image data of a subject. The system may also determine and/or analyze image data of a subject to assist in performing a procedure. Additionally, various systems may include those disclosed in U.S. Pat. Nos. 7,778,685; 7,742,629; 7,587,074; 7,321,677; and 6,980,675; and U.S. Pat App. Pub. No. 2013/0116739, 2011/0112398, 2006/0074285, and 2005/0008210; all incorporated herein by reference.

In various embodiments, a model can be created or generated of a subject based upon the image data. A system, such as the CardioGuide™ Implant System, may assist in creating the model. The model can include a three-dimensional model and/or a two-dimensional model based upon the image data. The model of the subject may include a model or be only a model of the vasculature of the subject. The model may be analyzed and/or used to suggest an appropriate lead and/or placement of a lead electrode for various therapies, such as a CRT.

According to various embodiments, a lead or other instrument can be positioned within a patient for assisting in performing a therapy on the patient. For example, a passive fixation lead may be positioned within a patient that interacts with various anatomical portions, such as internal walls of vessels of a vascular structure to assist in maintaining the lead at a selected location. According to various other embodiments, however, a lead can be positioned within an anatomy, such as a vasculature, that includes a portion that actively engages a portion of the anatomy. For example, a lead may include a member, such as a helical coil. At least a portion of the helical coil would pass into or move into a portion of a heart muscle or other muscle portion or fat portion to assist in "actively" maintaining the lead at a selected location. For example, the Attain Stability™ model 20066 lead, sold by Medtronic, Inc. includes a helically coiled wire portion that extends from the lead to engage a portion of anatomy. The active fixation portion may pass into or through a vasculature wall into various portions of the anatomy, including an epicardial fat or adipose tissue and/or myocardial tissue.

According to various embodiments, different leads, such as passive or active leads, can be positioned in appropriate portions of an anatomy, based upon an analysis of the anatomy. For example, a passive lead that includes a structure that interferes with or engages an internal wall or internal surface of a structure can be selected for appropriate procedures. According to various embodiments, however, the anatomy of a subject, such as a vasculature anatomy of a patient, passive fixation may not be appropriate or lead fixation may be enhanced by an active fixation within the subject. An active fixation can include a portion of a lead that engages a tissue of the anatomy through the vasculature wall.

According to various embodiments, a selection method can be used to determine whether or not an active fixation lead or a passive fixation lead is suggested to be used for a selected patient or subject. A method, as discussed further herein, can be executed in an algorithm or instructions based on an algorithm to assist in determining and/or suggesting a lead for fixation within a subject. According to various embodiments, the algorithm can be executed by a processor based upon instructions to assist in suggesting and/or determining a lead for placement within a subject. The processor may be a general purpose processor, such as a central processing unit, which is programmed by executing instructions. The instructions may be stored in a memory device integral with the processor or separate therefrom. Also, or alternatively, the processor may be an application specific integrated circuit (ASIC) or similar processor.

Once a procedure is determined, such as positioning an implantable medical device within a subject, placement of a lead that extends from the implanted medical device to a location within a subject can be determined. In particular, a lead generally provides stimulation to a selected location remote from the implanted medical device. For example, a ventricular simulation site (e.g. electrical stimulation) may be selected for stimulating a portion of a heart of a subject. The implanted medical device can provide power, control the stimulation, a return electrode or ground electrode, and other features. Nevertheless, a lead generally extends from the implanted medical device to a selected stimulation site.

According to various embodiments, a system can be used to determine or create a model of a subject. In various examples a two-dimensional (2D) imaging system, such as a fluoroscopy, may be used to acquire image data. As discussed above, a CardioGuide® System, as sold by Medtronic, Inc., can be used to analyze image data of a subject. The image data can include a venogram of the subject where a contrast agent is passed through a subject's vascular system and imaged with an x-ray system. Additional image data or alternative image data can be acquired by using a CT image device, an MRI device, or other appropriate imaging device. Nevertheless, the image data can be acquired of a subject and be used to determine various geometries of a subject, anatomy of a subject, and the like. For example, a model can be generated of a subject for further analysis. The model can be based on various features and can be used to identify or analyze a geometry of a subject.

With reference to FIG. 1, an image or model of a subject can be displayed on a display device 10 of a system 12. The system 12 can include a processor 14 and a memory system 16. It is understood, however, that the system 12 can also include transmission and receiving portions that allow for processing and memory to be separate from the system 12. Further, the system 12 can include an input, such as the screen 10 accepting a touch input and/or button or keypad input 18. The system 12 can be held by a hand 19 of a user allowing for ease of transport and/or manipulation of the system 12.

The display device 10 may display an image and/or model 20 of a subject. According to various embodiments, the model may be of a heart. The model 20 may illustrate various anatomical portions, including an aorta 21a, a left atrium 21b, a left ventricle 21c, a right ventricle 21d, and a right atrium 21e. Various other anatomical portions may include a coronary vasculature, including a coronary sinus (CS) 21f. A user, such as a surgeon, can identify on the model and/or image a target 24. The target 24 can be based upon various parameters, such as those generally known to the user and/or anatomical or other features of the subject. Nevertheless, a target can be identified using data of a subject to assist in determining an appropriate lead for positioning with the subject.

The target 24 may include at least one point in a target structure 25, such as a target vein that extends from the CS 21f. The CS 21f extends from a CSos 27 in the heart. The target vein 25 may extend at a "take-off" angle 29 from the CS 21f. Further, the target vein 25 may take-off from the CS 21f at a specific location relative to the CS section from the CSos 27, such as the first third or proximal third. Also, the take-off location may be relative to the anatomic location, such as posterior or superior.

Figure 2:
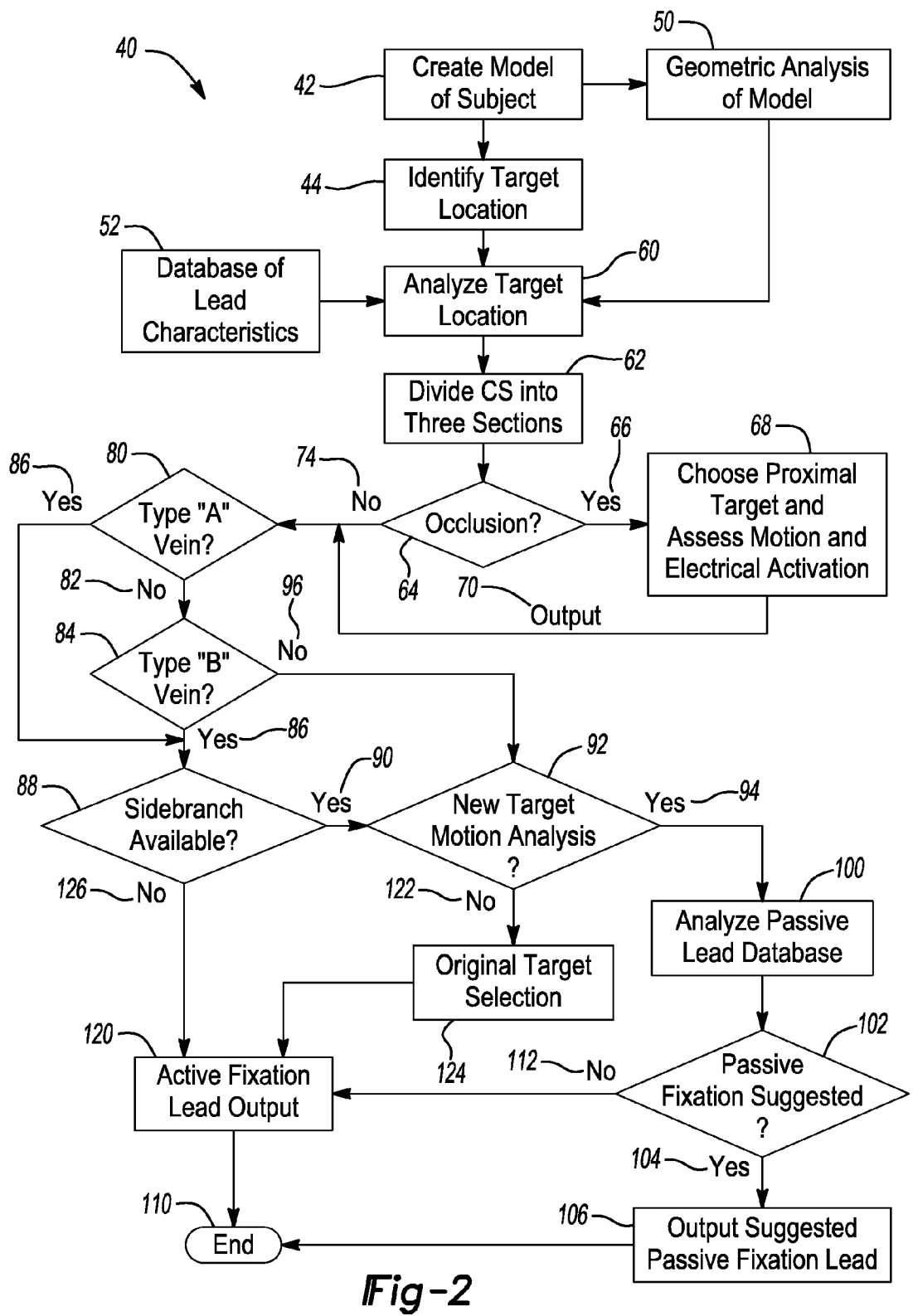
FIG. 2 is a flowchart.

With continued reference to FIG. 1, and in additional reference to FIG. 2, a method is illustrated in flowchart 40 that can be incorporated into instructions to be executed by the processor 14. The method 40 can be used to assist in identifying or suggesting a lead for implantation within the subject. The lead can be placed within the subject at the selected target 24 to assist in providing a therapy to the subject, such as a cardiac resynchronization therapy (CRT). Initially, the method 40 can create a three-dimensional model or a two-dimensional model of the subject. The model of the subject can include the coronary vasculature of the subject. Further, the model can include a geometry of the vasculature and a motion analysis. The motion analysis can include a motion map that includes physiological feedback on motion of the heart. For example, as is understood in the art, a subject's heart may move over time. Accordingly, the two-dimensional model or the three-dimensional model can include a time aspect to determine or illustrate movement of the heart over time.

The created model of the subject in block 42 may be used for various purposes or be followed up by various portions, as discussed further herein. Initially, as noted above, a target location can be identified in block 44. The target location may include or be placed in a target structure portion, such as a vein that takes off from the CS.

Once the model has been created in block 42, an analysis of the model can be made in block 50. The analysis of the model can include a geometrical analysis of the 2-D or 3-D model created in block 42. The analysis can further include various parameters such as determining or measuring a diameter at various locations along a vessel, a take-off angle (i.e., an angle that a first vessel branches from a second vessel), and various vessel lengths. The vessel lengths can be measurements between various locations of the vessel structure, such as between a take-off point and a termination point or target location. Further, the vessel lengths can include total and/or sectional distances, such as in relation to distances between electrodes of leads. Further, the vessel lengths can include distances relative to the identified target in block 44.

Additionally, the method 40 can include input from block 52 of a data base of lead characteristics. The lead characteristics can include predetermined or previously known measurements of leads. Example parameters include a lead body diameter, electrode distances, electrode to tip distances, function types, fixation types, cant or shaped dimensions, and other lead characteristics. Additional characteristics can include flexibility or stiffness of a lead, pushability of a lead, and other known or determined characteristics of leads. The information can be stored in the memory system, such as the memory 16 of the system 12. The database can be accessed in method 40 to assist in determining or suggesting a lead for implantation.

The identified target from block 44, the geometry analysis of the model from block 50, and the database of lead characteristics in block 52 can be input and used to analyze target location in block 60. In analyzing a target location, the angles at the target location or to reach the target location can be determined, distances from an entry point (e.g. a coronary sinus ostium or CS take-off location) can be determined, and diameters along the lead length can be determined. Appropriate calculation systems can include those disclosed in U.S. patent application Ser. No. 14/254, 288, entitled A method and System for Ranking Instruments, incorporated herein by reference. The analysis of the target location can be used for further suggestions or analysis, as discussed herein, and can be saved in the memory system 16. The analysis of the target location 60 can also include the analysis of the path or possible path from the entry point to the target location. Accordingly, analysis of the target location may not be an analysis of only the individual point of the identified target but may include analysis of the model, the target vein, etc.

Further, using the model created in block 42, the coronary sinus, or other selected vessel or tube portion, can be divided into a number of sections. For example, the CS 21f can be divided into three sections or types (e.g. Type A, Type B, or Type C) based on a right anterior oblique (RAO) projection of a venogram in block 62. The model may also be used to determine whether an occlusion is present from the entry point to the identified target in block 64. An occlusion may include a vessel or vessel portion that has a diameter that is less than a lead body diameter. It is understood that the vasculature of the human subject may stretch when a force is applied to it, such as passing a lead through it, therefore an "occlusive" diameter of the vessel relative to the lead body can be predetermined. For example, a vessel diameter that is not at least 50% of a lead diameter can be determined to be an occlusion. It is understood, however, that other appropriate ratios or percentages can be used, such as a vessel diameter of not at least 70%, not at least 80%, or not at least 90% can be determined to be occlusive vessels.

If an occlusion is determined to be present, a "yes" path 66 to choose a new target in block 68 can be followed. In determining or selecting a new target, a target based on the anatomical structure proximal of the occlusion can be selected. For example, the user can view the model with a determined location of an occlusion, and choose a target based on the anatomical structure proximal or closer to an entry point relative to the occlusive portion. Another option to determine an alternative target could be based on a motion analysis and/or assessment of synchronous changes (e.g., electrical) can be made. That is, the new target will generally need to be able to apply a similar therapy to the subject as the original target. Accordingly, an analysis of motion of the heart based upon possible stimulation from an IMD can be analyzed to determine if the new target is appropriate relative to the subject. The user can also determine a location based on the user's anatomical assessment and conduct a motion analysis and/or assessment of synchronous changes (e.g., electrical) for this specific location afterwards.

Once a new target has been determined in block 68, an output path 70 can be followed to a "no" path 74 from the occlusion decision block 64. As noted above, a lead that can be implanted into a subject may have various characteristics. For example, an active fixation lead is a lead that includes a portion that engages and/or passes into tissue of a subject. A passive fixation lead generally engages an internal wall or internal surface of the vessel and may be "wedged" into position. Accordingly, an analysis of the model created in block 42 can be used to determine an appropriateness of an active lead or a passive lead. Accordingly, after determining that the target is not occluded, the no path 74 can lead to an analysis of the vein or vessel type.

A first decision block is whether a vein or vessel is a type-A vein in block 80. As noted above, an anatomy of a subject can include various types of vasculature or vein structures. The types of veins can be based upon or be defined in light of geometry of the subject's vasculature. According to various embodiments, such as that disclosed in Biffi et al. noted above, vessels may include or define various vein structures. Vein structures that are present in a subject can assist in determining and/or suggesting an appropriate lead for placement at the target location. Accordingly, a decision block of whether a vein is a type-A vein can be made.

A type-A vein may be a vein that takes off or branches from the coronary sinus in the proximal one-third of the coronary sinus. The coronary sinus 21f, as is generally understood in the art, initiates from the coronary sinus ostium 27 and extends over or away from the coronary sinus ostium. Various vasculatures extend from the coronary sinus. The vein being analyzed and/or determined to be a type-A vein or a non-type A vein is the target vein, that is the vein that includes the target identified in block 44.

If it is determined that the target location is in the vein is not a type-A vein, a no path 82 can be followed to a second decision block of whether a vein is a type-B vein. A type-B vein is a vein that is more distal or posterior than a type-A vein, or is not as proximal of the CSos and can include a take-off or bifurcation angle of greater than 80°. A bifurcation angle that is greater than 80° can include a target vein that is not substantially angled or does not include a sharp angle relative to the coronary sinus. Accordingly, a lower and/or substantially flat angle is defined relative to the coronary sinus from the target vein.

If the target vein is a type-A vein or a type-B vein, a yes path 86 can be followed to a decision block of whether a side branch from the target vein is available in block 88. A side branch may be available if the side-branch has a length that is at least about 8 millimeters (mm), including about 12 mm, including about 10 mm in length from the initial vein target. Further, the side branch must be determined to not be occlusive according to the same parameters in block 64. If the side branch is determined to be present, a yes path 90 can be followed to a new target motion analysis determination in block 92. If a new target motion analysis in block 92 is shown to be positive, such as a similar analysis as the geometry analysis of block 50 and the new target analysis of block 68, a yes-path 94 can be followed. A new motion analysis in block 92, however, may not be necessary if the analysis from block 68 is informative regarding the side branch, such as regarding size, motion, etc. The yes path 94 combines or goes to an analysis of a passive fixation lead database in block 100. A no path 96 from the type-B vein determination block 84 also goes to the analysis of a passive fixation lead in block 100 if the target motion analysis in block 92 is positive.

In the analyze passive lead database in block 100, a determination and/or evaluation of leads that do not include active fixations can be made. The determination can include identifying or analyzing the target location relative to passive leads that are used to engage internal surfaces of vasculature for stability. Analysis can include various analyses, such as those disclosed in U.S. patent application Ser. No. 14/254,288, entitled A method and System for Ranking Instruments incorporated herein by reference. Accordingly, a passive lead fixation can be analyzed for possible suggestion, and suggestion of possible specific leads, when it is determined that the target vein is not a type-A vein, not a type-B vein, and/or if a side branch is present for appropriate fixation of a passive lead. Analysis of passive lead database in block 100 can then lead to a determination block of whether passive fixation is appropriate or is suggested in block 102.

Passive fixation can be suggested in block 102 based upon various parameters, including those discussed above. The parameters can include a determining the minimum vessel diameter at the target location relative to a diameter lead body at the target location. The passive fixation, also referred to as "wedging", can be analyzed based upon a geometry of the lead, including that input from the database of lead characteristics in block 52, and an analysis of the geometry of the model in block 50. If it is determined that the passive fixation is suggested in block 102, a yes path 104 can be followed and a suggested passive fixation lead can be made in block 106. The suggestion of a passive lead can be made as an output, such as an output on the display device 10 discussed above. The output can include a graphical, numerical, written, or other appropriate output. The output can identify one or more leads for selection by a user. Further, the suggested lead can include various characteristics and information such as the relative lead diameter to the vessel diameter and other appropriate information.

If, after the determination block 102 of whether a passive fixation is suggested, it is determined that passive fixation is not suggested, then a no-path 112 can be followed to an active fixation analysis output in block 120. By following the no-path 112 after determination that a passive fixation is not suggested in block 102, one or more active fixation leads can be suggested in block 120. Again, the output from the active fixation lead output of block 120 can be similar to that for the output of the suggested passive fixation lead, but include suggested active fixation leads. Further, the active fixation lead can include a determination or output of a position of a helix or active fixation member relative to the electrodes in the lead, active fixation site location, and other appropriate information. Accordingly, one or more active fixation leads can be suggested and output in block 120 for selection by a user.

The active fixation lead output in block 120 can also be reached if a no-path 122 from the new target motion analysis in block 92 is followed to an original target selection in block 124. Accordingly, if the new target motion analysis in block 92 does not lead to a positive result, the original target location can be reintroduced or accepted in block 124 and an active fixation lead output can be suggested in block 120. Further a no-path 126 can be followed from the decision block of whether a side branch is available in block 88. Accordingly, an active fixation lead output in block 120 can be based upon various analyses and determinations, including that a side branch is not available in block 88, that a new target motion analysis is not acceptable in block 92, or that a passive fixation is not suggested in block 102.

Regardless of the determination of an active fixation lead or a passive fixation lead the method can end in block 110. Ending in block 110 can end the method 40, by providing suggested leads to a user. The suggestion of leads can be the suggestion of more than one lead to be selected by a user based upon various further analyses, such as experience of a user. Further, the method 40 can be used to suggest a lead that is selected by a user for implantation. Accordingly, it is understood, that a procedure that includes the method 40 can end with the suggestion of a lead and then the implantation of the suggested lead and/or suggested lead based upon the suggestions. Accordingly, a procedure can include the method 40 for selecting a lead that is then implanted in a patient.

It is further understood that the timing of the method 40 can be at any appropriate time. For example, a user can obtain image analysis of a subject and the lead can be suggested at any appropriate time. The image analysis can occur prior to an implantation procedure time, substantially concurrent, or immediately before an implantation time, or at any appropriate time. For example, a subject may be imaged using an appropriate imaging system at a first time. At the first time a diagnosis can be made, such as selecting a cardiac resynchronization of therapy. The image data can be used to analyze the subject according to the method 40 for a determination of a target location, a lead suggestion, and other appropriate pre-procedure planning. Following the imaging and performing of the method 40, such as by hours, days, weeks, or any appropriate period, a subject can then implanted with a lead, including the suggested lead. The lead can be based upon the suggestion from the method 40 as discussed above.

Further, it is understood that the method 40 need not be limited to a cardiac resynchronization therapy. For example, the method 40 can be used to identify appropriate locations for various lead implantation, such as for nerve stimulation (e.g., spinal stimulation), pacing, or defibrillation therapies, or other appropriate therapies. Further, as noted above, the method 40 can be used in an appropriate manner to assist in identifying placement and positioning of instruments in non-anatomical and non-human subjects. For example, the method 40 may be used to assist in determining placement of a specific, selected or suggested instrument within a tube instrument (e.g., a heat exchange system).

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

What is claimed is:

1. A method of selecting an instrument for placement within a subject, comprising:
   preparing image data of the subject;
   analyzing a geometry of a subject structure in the prepared image data;
   determining a type of structure within the subject based on the analyzed geometry of the subject structure;
   evaluating, by a processor executing instructions, an instrument database including parameters of a plurality of instruments in the instrument database based on the determined type of structure of the subject; and
   displaying on a display device viewable by a user at least one suggested instrument based on the evaluation of the instrument database and based on the determined type of structure within the subject.

2. The method of claim 1, wherein preparing the image data of the subject includes creating a model of the subject based on the image data.

3. The method of claim 2, further comprising:
   accessing the image data of the subject.

4. The method of claim 3, wherein the image data includes at least one of a venogram of a vasculature, magnetic resonance image data, computed tomography image data, or combinations thereof.

5. The method of claim 2, further comprising:
   identifying a coronary sinus in the created model; and
   dividing the coronary sinus into three sections.

6. The method of claim 5, further comprising:
   inputting a first target location as at least one point in the created model; and
   determining a branch vessel from the coronary sinus including the first target location.

7. The method of claim 6, wherein determining the type of structure includes analyzing the determined branch vessel relative at least one section of the three sections.

8. The method of claim 6, wherein determining the type of structure includes determining a take-off angle of the determined branch vessel from the identified coronary sinus.

9. The method of claim 8, wherein evaluating the instrument database includes determining whether an active fixation lead is suggested based on at least one of the analyzed determined branch vessel location relative at least one section of the three sections or the determined take-off angle of the determined branch vessel from the identifying coronary sinus.

10. The method of claim 9, wherein evaluating the instrument database includes evaluating whether a passive fixation lead is suggested prior to determining whether the active fixation lead is suggested.

11. The method of claim 10, further comprising:
    selecting a second target location;
    inputting the second target location; and
    evaluating the created model relative to the second target location.

12. The method of claim 1, wherein evaluating the instrument database includes determining whether an active fixation lead is suggested based on at least one of the analyzed determined branch vessel location relative to at least one section of the three sections or the determined take-off angle of the determined branch vessel from the identifying coronary sinus.

13. A method of selecting an instrument for placement within a subject, comprising:
    creating a model of at least a structure in a subject with image data of the subject;

analyzing a geometry of the structure in the created model;
identifying a coronary sinus in the created model and divide the coronary sinus into three sections along a length of the coronary sinus;
inputting a target location to a processor;
determining, by the processor executing instructions, a type of a target vein that includes the target location based on the analyzed geometry of the subject;
evaluating, by a processor executing instructions, an instrument database including parameters of a plurality of lead instruments in the instrument database and based on the determined type of target vein of the subject; and
displaying on a display device at least one suggested lead instrument based on the evaluation of the instrument database and the determined type of the target vein within the subject.

14. The method of claim 13, wherein determining the type of the target vein includes:
determining a take-off location of the target vein from the identified coronary sinus; and
determining a take-off angle of the target vein from the coronary sinus.

15. The method of claim 14, wherein determining the type of the target vein includes determining that the target vein is a type-A vein or a type-B vein if the determined take off location is within a proximal one-third of the coronary sinus or the determined take-off angle is greater than eighty degrees.

16. The method of claim 15, further comprising:
determining if a sidebranch is present on the target vein; and
determining if a second target location in the sidebranch is acceptable for a passive fixation or not acceptable for passive fixation.

17. The method of claim 16, wherein the parameters of a plurality of instruments includes an active fixation parameter and a passive fixation parameter and outputting the at least one suggested lead instrument includes outputting a suggested active fixation lead when the determination is that the target vein is the type-A vein or the type-B vein and a determination of the second target location is not acceptable for passive fixation.

18. The method of claim 13, further comprising:
determining if an occlusion is present in the created model prior to the target location, and if an occlusion is present selecting a new target location different from the first target location.

19. A system for selecting an instrument for placement within a subject, comprising:

a display device configured to display a created model;
an input to allow for input; and
a processor system configured to execute instructions to:
create a model of at least a structure in a subject with image data of the subject;
analyze a geometry of the structure in the created model;
identify a coronary sinus in the created model and divide the coronary sinus into three sections;
receive an input of a target location in a target vein;
determine a type of the target vein that includes the target location based on the analyzed geometry of the subject;
evaluate parameters of a plurality of instruments in an instrument database based on the determined type of structure of the target vein; and
output at least one suggested lead instrument based on the evaluation of the parameters and the determined type of the target vein within the subject;
wherein the display device is further configured to display the output.

20. The system of claim 19, wherein in executing instructions to determine the type of the target vein that includes the target location based on the analyzed geometry of the subject, an evaluation of a take-off location of the target vein from the identified coronary sinus and an evaluation of a take-off angle of the target vein from the coronary sinus is made;
wherein the target vein is a type-A vein or a type-B vein if the determined take off location is within a proximal one-third of the coronary sinus or the determined take-off angle is greater than eighty degrees.

21. The method of claim 20, wherein outputting the at least one suggested instrument includes outputting a suggested active fixation lead when the determination is that the target vein is the type-A or the type-B and a determination of at least a second target location is not acceptable for passive fixation.

22. The method of claim 13, wherein determining the type of the target vein includes classifying the vein as a Type-A or a Type-B vein if the vein has a take off in the proximal one-third of the coronary sinus and includes a take-off or bifurcation angle of greater than 80°,
wherein outputting on a display device at least one suggested lead instrument based on the evaluation of the instrument database and the determined type of the target vein within the subject includes suggesting an active fixation if no sidebranch target vein is available.

* * * * *